(12) United States Patent
Angara et al.

(10) Patent No.: US 10,099,058 B2
(45) Date of Patent: Oct. 16, 2018

(54) SYSTEMS AND METHODS FOR TRANSCUTANEOUS CONTROL OF IMPLANTABLE PULSE GENERATORS FOR NEUROMODULATION

(71) Applicant: CIRTEC MEDICAL CORP., Brooklyn Park, MN (US)

(72) Inventors: Raghavendra Angara, Exton, PA (US); Miles Curtis, Philadelphia, PA (US); Christopher Biele, King of Prussia, PA (US); Saif Khalil, Wayne, PA (US); Jason Highsmith, Charleston, SC (US)

(73) Assignee: Cirtec Medical Corp., Brooklyn Park, MN (US)

( * ) Notice: Subject to any disclaimer, the term of this patent is extended or adjusted under 35 U.S.C. 154(b) by 236 days.

(21) Appl. No.: 15/044,209

(22) Filed: Feb. 16, 2016

(65) Prior Publication Data

US 2016/0271405 A1     Sep. 22, 2016

Related U.S. Application Data

(60) Provisional application No. 62/116,751, filed on Feb. 16, 2015.

(51) Int. Cl.
*A61N 1/00* (2006.01)
*A61N 1/372* (2006.01)
*A61N 1/05* (2006.01)
*A61N 1/36* (2006.01)

(52) U.S. Cl.
CPC ....... *A61N 1/37217* (2013.01); *A61N 1/0551* (2013.01); *A61N 1/36125* (2013.01); *A61N 1/37247* (2013.01)

(58) Field of Classification Search
CPC .......................... A61N 1/37217; A61N 1/0551
USPC .......................................................... 607/60
See application file for complete search history.

(56) References Cited

U.S. PATENT DOCUMENTS

2013/0079849 A1*   3/2013   Perryman .......... A61N 1/37223
                                                    607/60

* cited by examiner

*Primary Examiner* — Nadia A Mahmood

(57) ABSTRACT

Systems, devices and methods for providing neuromodulation are provided. One such system can include an implantable pulse generator. The implantable pulse generator can include a circuit board having a microcontroller that generates signals that are input into an ASIC. The ASIC serves as pulse generator that allows electrical pulses to be outputted into leads. The implantable pulse generator is capable of receiving and/or generating signals either via a wireless communication (e.g., a wireless remote control), a touching force (e.g., pressure from a finger), a motion sensor or any combination of the above.

15 Claims, 7 Drawing Sheets

SYSTEMS AND METHODS FOR TRANSCUTANEOUS CONTROL OF IMPLANTABLE PULSE GENERATORS FOR NEUROMODULATION

REFERENCE TO RELATED APPLICATIONS

The present application is a nonprovisional application claiming priority to provisional U.S. application No. 62/116,751, filed Feb. 16, 2015, which is hereby incorporated by reference in its entirety.

FIELD OF THE INVENTION

The present application is generally directed to systems, devices and methods for providing neuromodulation.

BACKGROUND OF THE INVENTION

Neuromodulation is a treatment that delivers either electricity or drugs to nerves in order to change their activity. Neuromodulation is the name for an overall category of treatment, one that can be used for a variety of diseases and symptoms. For example, neuromodulation can be used to treat spinal cord damage, headaches, Parkinson's disease, chronic back pain and even deafness.

Neuromodulation is used to treat and enhance quality of life in individuals who suffer severe chronic illness due to persistent pain, spasticity, movement disorders, epilepsy, ischaemic, cardiac, bowel and bladder dysfunction, spinal injury, visual, auditory, and specific psychiatric disorders. Neuromodulation is typically not used to remove the source of pain. Rather, it is typically used to mask pain.

To enable neuromodulation, an implantable pulse generator (IPG) can be implanted into a patient. The implantable pulse generator can generate electrical pulses for therapeutic purposes. It is desirable to have different systems and methods that enable neuromodulation and control the output parameters of an implantable pulse generator.

SUMMARY OF THE INVENTION

Various systems, devices and methods related to neuromodulation are provided. In some embodiments, a system for exerting pulses to a targeted site within a body comprises an implantable pulse generator. The implantable pulse generator comprises a casing housing a circuit board, wherein the circuit board contains circuitry comprising a microcontroller and an Application Specific Integrated Circuit or ASIC, wherein the microcontroller is configured to receive signals generated from a wireless remote control and a touching force, wherein the ASIC is configured to receive data from the microcontroller to generate electrical signals. In addition, the implantable pulse generator comprises a lead contact assembly operably connected to the ASIC, wherein the lead contact assembly comprises a plurality of leads that are used to carry electrical signals from the IPG to the targeted site within the body.

In some embodiments, a system for exerting pulses to a targeted site within a body comprises an implantable pulse generator. The implantable pulse generator comprises a casing housing a circuit board, wherein the circuit board contains circuitry comprising a microcontroller and an Application Specific Integrated Circuit or ASIC, wherein the microcontroller is configured to receive signals generated from a touching force, wherein the ASIC is configured to receive data from the microcontroller to generate electrical signals. In addition, the implantable pulse generator comprises a lead contact assembly operably connected to the ASIC, wherein the lead contact assembly comprises a plurality of leads that are used to carry electrical signals from the IPG to the targeted site within the body.

BRIEF DESCRIPTION OF THE DRAWINGS

The invention will be more readily understood with reference to the embodiments thereof illustrated in the attached figures, in which.

DETAILED DESCRIPTION OF THE ILLUSTRATED EMBODIMENTS

Figure 1:
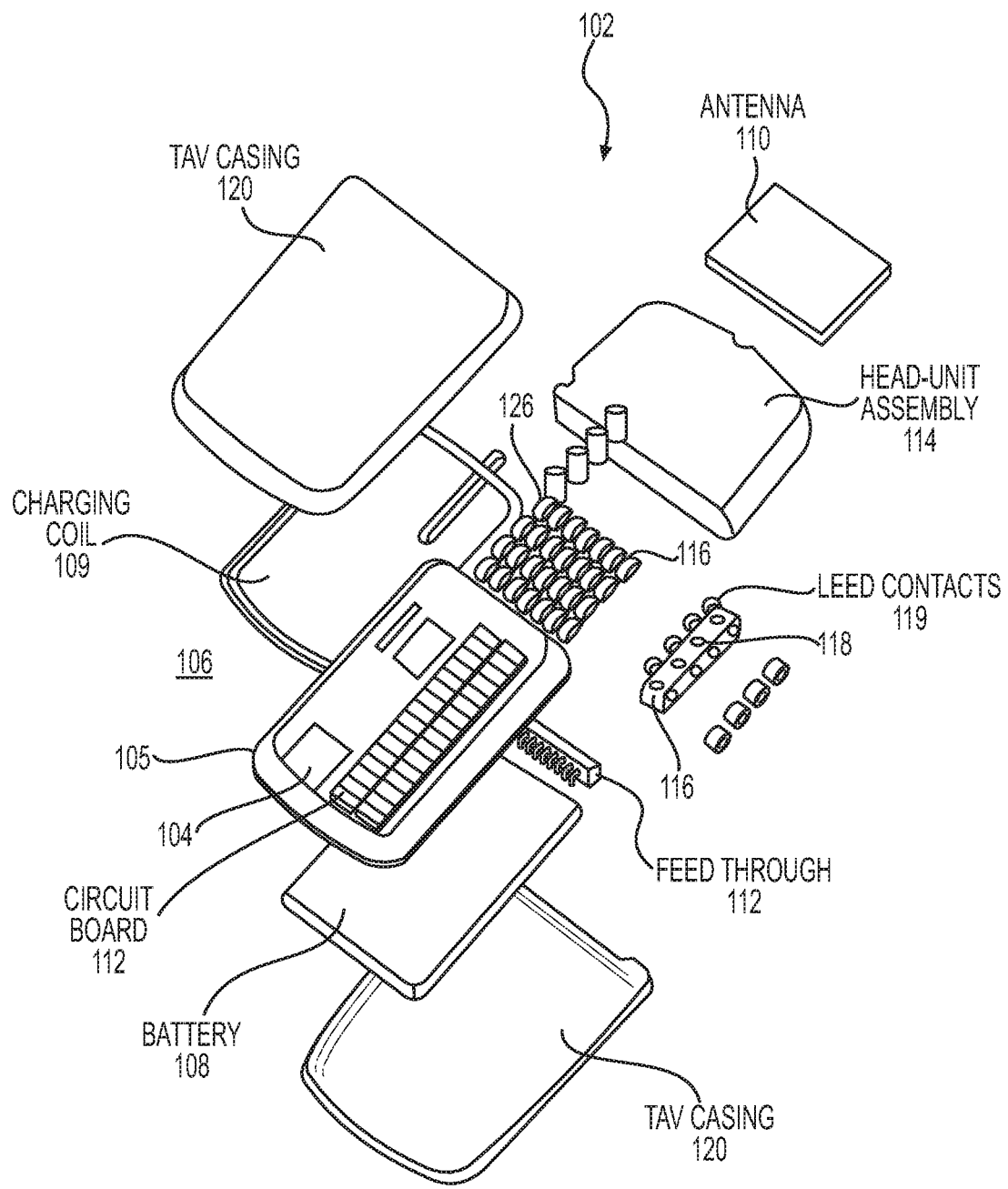
FIG. 1 shows one example of an IPG that can be controlled by wireless remote and which can benefit from the addition of touch and motion sensors.

Embodiments of the invention will now be described. The following detailed description of the invention is not intended to be illustrative of all embodiments. In describing embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

The present application relates to systems and methods for transcutaneous control of implantable pulse generators (IPGs) used in neuromodulation. The IPGs can be used to treat a variety of illnesses, including but not limited to persistent pain, spasticity, movement disorders, epilepsy, ischaemic, cardiac, bowel and bladder dysfunction, spinal injury, visual, auditory, and specific psychiatric disorders. In some embodiments, an IPG is used for spinal cord stimulation (SCS), whereby the IPG sends pulsed electrical signals to the spinal cord to control chronic pain.

An IPG can be used to deliver electrical pulses to treat chronic pain. In some embodiments, an IPG is implanted subcutaneously in a patient. The IPG can be attached to stimulation electrodes that deliver electrical pulses to specific sites. For example, in spinal cord stimulation, one or more electrodes can be implanted directly into an epidural space.

An IPG can serve multiple functions. In some embodiments, an IPG can consist of a battery and a circuit board that provides and controls the currents of electrical stimulation. In some embodiments, the IPG can comprise a microcontroller transceiver component and an application-specific integrated circuit (ASIC) component. The transceiver can be used to receive, decode and execute commands and requests from a remote control. These commands and requests can be passed onto the ASIC. The ASIC receives the digital data from the microcontroller and performs the entire signal processing to generate the signals necessary for stimulation. In some embodiments, the ASIC serves as a pulse generator. These signals are then passed onto the stimulation electrodes, which can then deliver pulses to a desired site.

Devices such as IPGs can be controlled wirelessly by external hand held remote controls outside of the body. In some embodiments, these remotes can communicate with the IPG by radiofrequency or induction. The remotes can be used to perform a number of functions, including but not limited to turning stimulation ON and OFF, increasing or decreasing the amplitude of stimulation, and changing programs.

While IPGs have been successfully controlled by remote controls, the use of remote controls is not always practical. There may be instances when the wireless connection between the remote control and the IPG goes out. In addition, there may be times when using a remote control, such as in heavy rain, in the shower, or in a swimming pool, may not be feasible. Furthermore, a patient may simply forget to bring a remote control with them.

Accordingly, the present application discloses systems and methods for controlling implanted devices, such as IPGs, in ways other than wireless remote controls. In particular, the present application discloses novel systems and methods for communicating with IPGs whereby touch sensors and/or motion sensors will be used in the IPGs, and the communication to control the stimulation is by touch and motion gestures. In some embodiments, the communication to control the stimulation is transcutaneous.

FIG. 1 shows one example of an IPG that can be controlled by wireless remote and which can benefit from the addition of touch and motion sensors. In some embodiments, the IPG 102 comprises a casing 120 that houses a battery 108, a circuit board 105, and charging coil 109. The circuit board 105 contains circuitry including a transceiver 104, ASIC 106, and output capacitors 112. The IPG 102 further includes an epoxy header 114 which houses a lead contact assembly 116, locking housing 118 and antenna 110. The lead contact assembly 116 comprises a plurality of stimulation leads that are used to carry electrical signals from the IPG to targeted stimulation areas. In some embodiments, the leads of the lead contact assembly 116 are secured to the IPG 102 via one or more set screws 119 that operate within the locking housing 118. The internal electronics (e.g., from the circuit board 105) are connected to the components within the epoxy header 114 through a hermetic feedthrough 122. The IPG 102 further comprises electrical contacts 126 that can form an electrical connection between the circuit board and the lead contacts. In some embodiments, the electrical contacts 126 can be arranged in four rows of eight contacts.

The IPG in FIG. 1 can benefit from the addition of touch and motion sensors. In particular, one or more touch and motion sensors can advantageously be added, including piezoelectric sensors, magnetostrictive sensors, accelerometers, and gyroscopes. In some embodiments, the motion sensors can comprise MEMS-based accelerometers. Each of these sensors provides added benefits to the IPG. A touch gesture performed on the surface of a patient's body can be read by piezo-type sensors mounted on the surface of the IPG. A motion or impact gesture performed on the surface of a patient's body can be read by accelerometers mounted inside the IPG. The IPG then interprets these gestures by using electronic circuits and software algorithms programmed in them.

Figure 2:
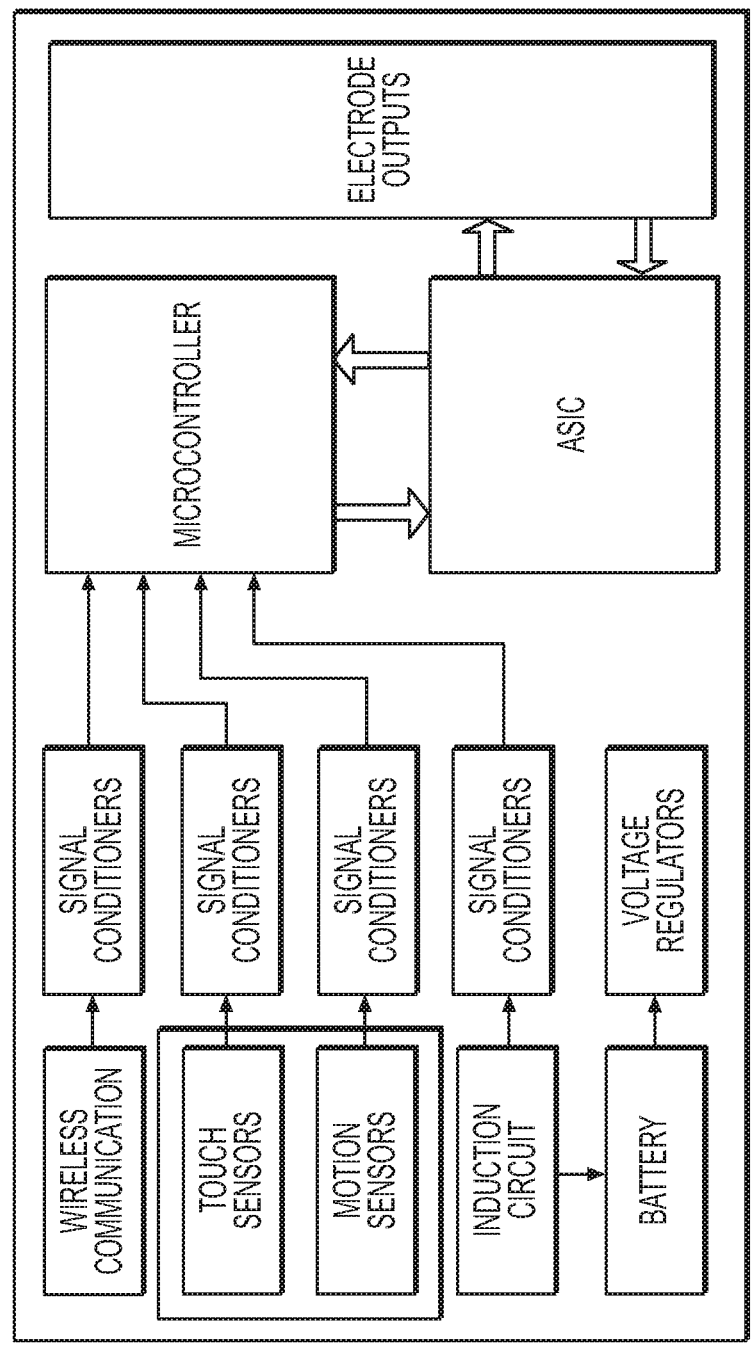
FIG. 2 shows a block diagram of an IPG of a neuromodulation device having both wireless capabilities and touch and motion sensors in accordance with some embodiments.

FIG. 2 shows a block diagram of an IPG of a neuromodulation device having both wireless capabilities and touch and motion sensors in accordance with some embodiments. In some embodiments, the IPG will have a wireless module (similar to as shown in FIG. 1) for wireless communication and induction modular for wireless charging of the battery. In addition to these modules, the IPG also includes touch sensors and/or motion sensors. In some embodiments, the IPG includes only touch or only motion sensors, while in other embodiments, it includes both. In addition, in some embodiments, multiple touch and/or motion sensors can be included in the IPG.

As shown in the block diagram in FIG. 2, the touch and motion sensors output analog voltage (or current) corresponding to the magnitude of the input. The output signals from the touch and motion sensors are fed into one or more signal conditioning circuits to scale them to a voltage range readable by one or more microcontrollers. In some embodiments, as shown in FIG. 2, each of the touch sensors and motion sensors has its own associated signal conditioning circuits, which are then fed into a single microcontroller. The scaled sensor output can be read by using external analog to digital converter modules, or by built-in modules within the microcontroller itself. Commands can then be passed on from the microcontroller to the ASIC, whereby one or more electrode outputs can be generated.

Figure 3:
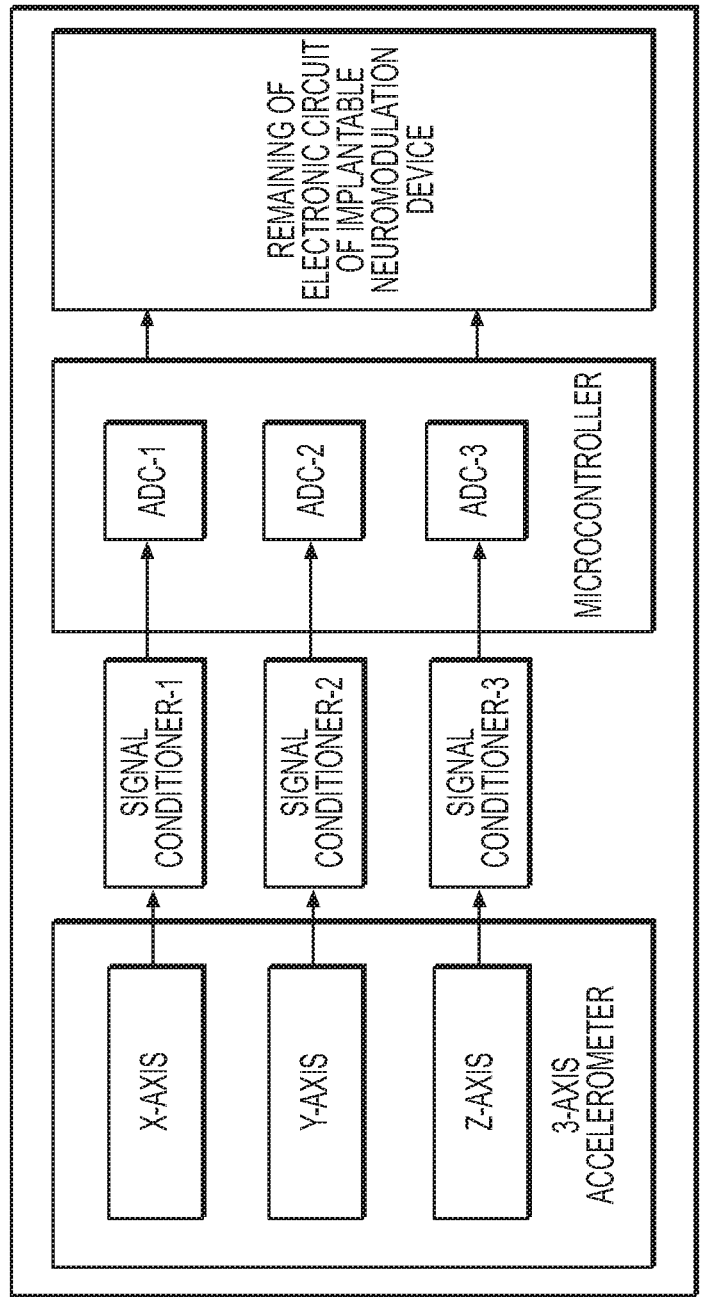
FIG. 3 shows a block diagram of a motion sensor that can be incorporated into the IPG shown in FIG. 2.

FIG. 3 shows a block diagram of a motion sensor that can be incorporated into the IPG shown in FIG. 2. In some embodiments, the motion sensor comprises an accelerometer (e.g., a 3-axis accelerometer) or an impact sensor that can be used to sense tapping gestures from a human (e.g., a doctor or the patient himself). When the user taps in a certain pattern on the surface of the skin where the neuromodulation device is implanted, the electronics inside will detect the tapping gesture and perform the task related to the tapping gesture. As an example, a single tap can be used to turn OFF the stimulation and a quick double tap can be used to turn ON the stimulation. A series of multiple taps with decreasing impact can be used to decrease the stimulation amplitude. Impacts in other axes can be used to communicate other controls such as changing the program. In some embodiments, as shown in the circuits in FIG. 3, either a microcontroller that can independently read multiple analog signals or a multiplexer can be used to read the sensors one after the other selectively.

In some embodiments, the IPG will advantageously be protected against accidental pushes of the touch or motion sensor. For example, the IPG can include multiple sensors such that in order to modify an electric pulse, the multiple sensors would need to be pushed in an alternating pattern. This advantageously reduces the likelihood that the IPG will be inadvertently pushed (e.g., by an individual bumping into another), thereby having better control over the pulses generated by the IPG. In other embodiments, one or more sensors can be programmed to have a pressure threshold which must be reached before any action is taken. These safeguards can be used, either alone or in combination, to reduce the risk of inadvertent actuation of the IPG.

Figure 4:
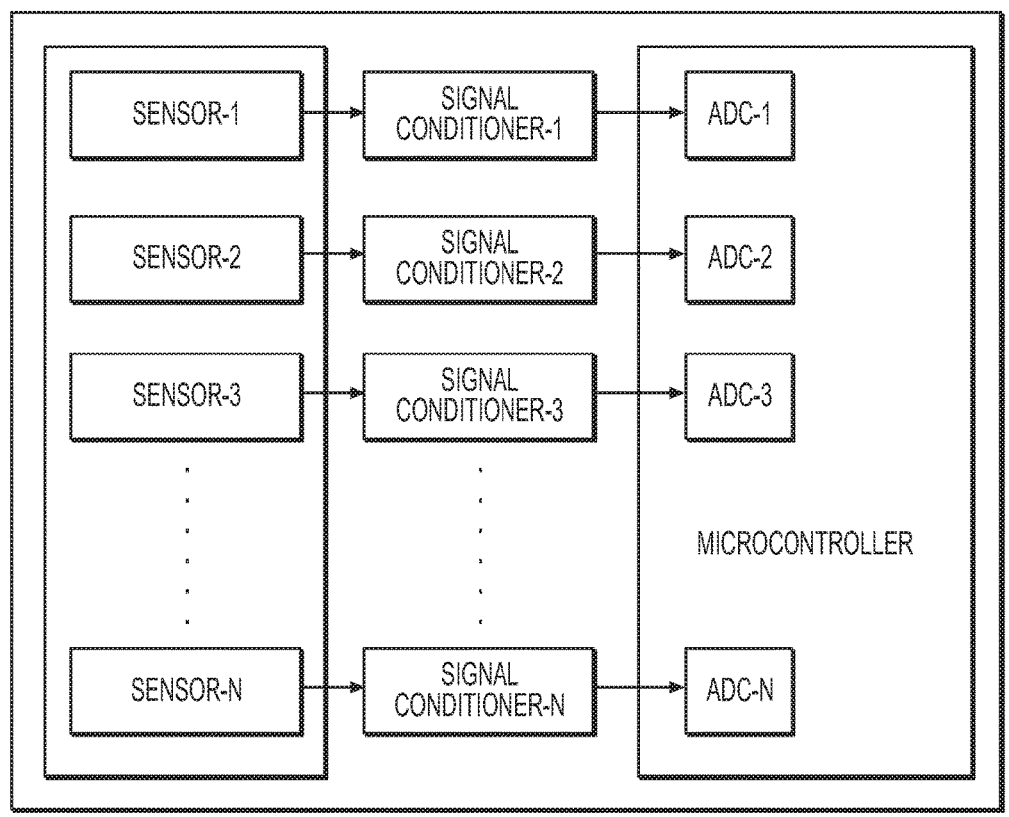
FIG. 4 shows a block diagram whereby multiple sensors are provided in a single device.

FIG. 4 shows a block diagram whereby multiple sensors are provided in a single device. Advantageously, the use of multiple sensors will make the touch controls easier. In some embodiments, each sensor can be fed through a signal conditioner and read through a dedicated analog to digital converter. In other embodiments, each sensor can be read selectively using a multiplexer.

Figure 5:
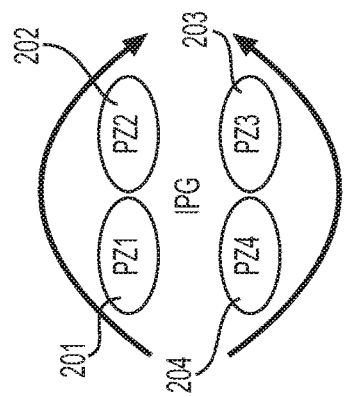
FIG. 5 shows an IPG utilizing four touch sensors.

FIG. 5 shows an IPG utilizing four touch sensors 201, 202, 203, 204. The four sensors are arranged such that they can be sequentially touched in a clockwise manner. In some embodiments, to actuate a signal from the IPG, a clockwise sweeping motion over one or more of the touch sensors 201, 202, 203, 204 can be used.

Figure 6:
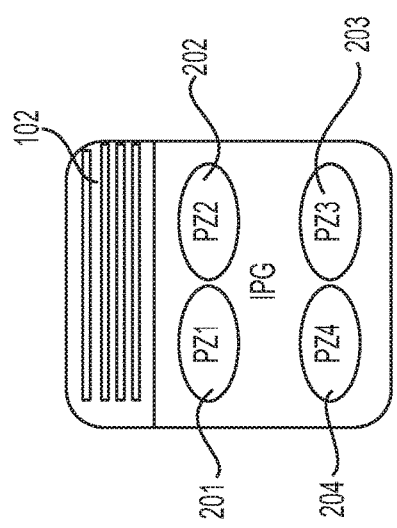
FIG. 6 illustrates the process of a user providing a clockwise sweeping gesture around the four touch sensors to generate an output.
Figure 7:
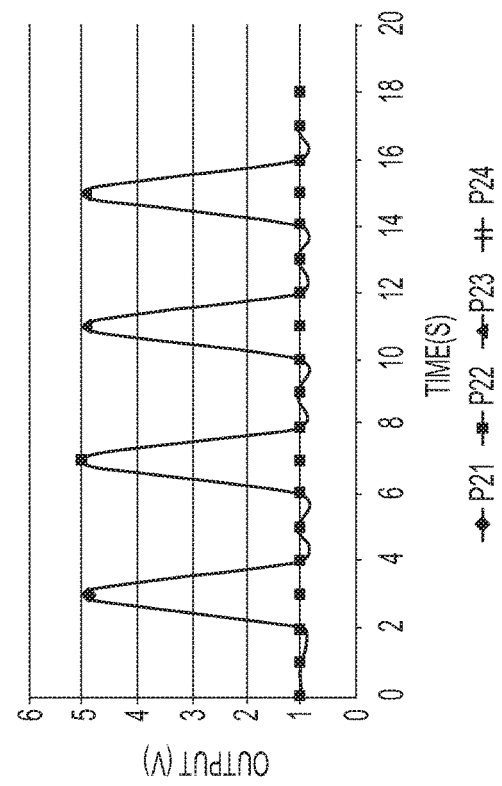
FIG. 7 shows a chart of a voltage output as sensors are touched in a sequential, counterclockwise manner in accordance with one embodiment.

FIG. 6 illustrates the process of a user providing a clockwise sweeping gesture around the four touch sensors 201, 202, 203, 204 to generate an output. The four touch sensors can be touched sequentially to produce an output, with sensor 201 being excited first, followed by sensor 202, 203 and then 204. In some embodiments, more than one rotation of the four touch sensors 201, 202, 203, 204 is needed to generate an output. In other embodiments, a single complete rotation is needed to produce an output, but additional rotations can modify the output. For example, in some embodiments, a clockwise sweep past a single rotation can increase the amplitude of a stimulation. In other embodiments, such a clockwise sweep can decrease the amplitude of a stimulation. FIG. 7 shows a chart of a voltage output as the sensors 201, 202, 203, 204 are touched in a sequential, counterclockwise manner in accordance with one embodiment.

Figure 8:
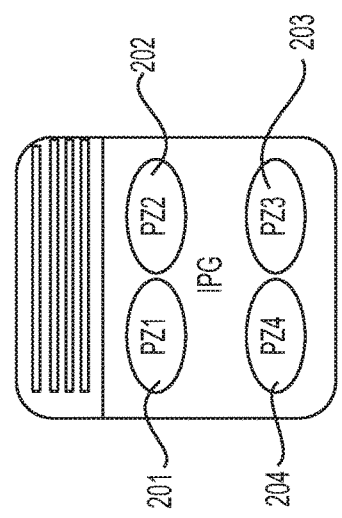
FIG. 8 shows an IPG utilizing four touch sensors.

FIG. 8 shows an IPG utilizing four touch sensors 201, 202, 203, 204. The four sensors are arranged such that they can be sequentially touched in a counter clockwise manner. In some embodiments, to actuate a signal from the IPG, a counter clockwise sweeping motion over one or more of the touch sensors 201, 202, 203, 204 can be used.

Figure 9:
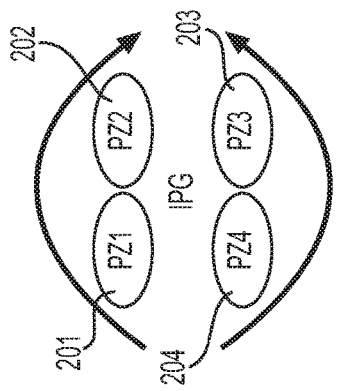
FIG. 9 illustrates the process of a user providing a counter clockwise sweeping gesture around the four touch sensors to generate an output.
Figure 10:
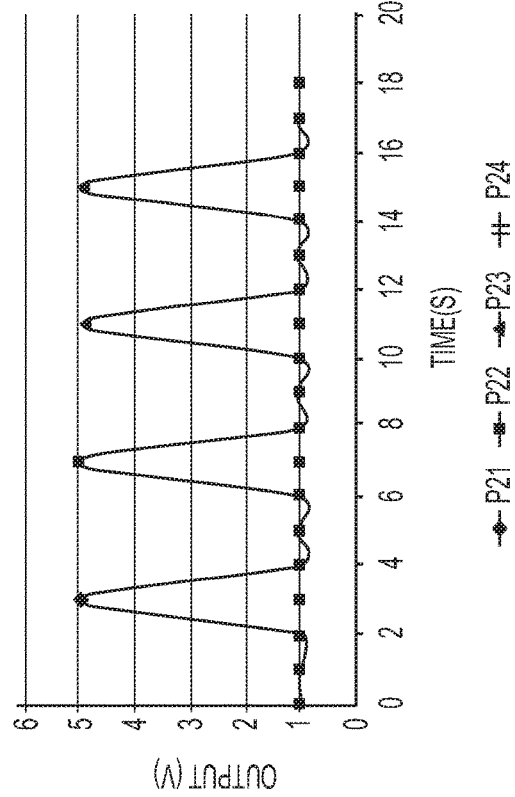
FIG. 10 shows a chart of a voltage output as sensors are touched in a sequential, counterclockwise manner in accordance with one embodiment.

FIG. 9 illustrates the process of a user providing a counter clockwise sweeping gesture around the four touch sensors 201, 202, 203, 204 to generate an output. The four touch sensors can be touched sequentially to produce an output, with sensor 204 being excited first, followed by sensor 203, 202 and then 201. In some embodiments, more than one rotation of the four touch sensors 201, 202, 203, 204 is needed to generate an output. In other embodiments, a single complete rotation is needed to produce an output, but additional rotations can modify the output. For example, in some embodiments, a counter clockwise sweep past a single rotation can decrease the amplitude of a stimulation. In other embodiments, such a counter clockwise sweep can increase the amplitude of a stimulation. FIG. 10 shows a chart of a voltage output as the sensors 201, 202, 203, 204 are touched in a sequential, counter counterclockwise manner in accordance with one embodiment.

Figure 11:
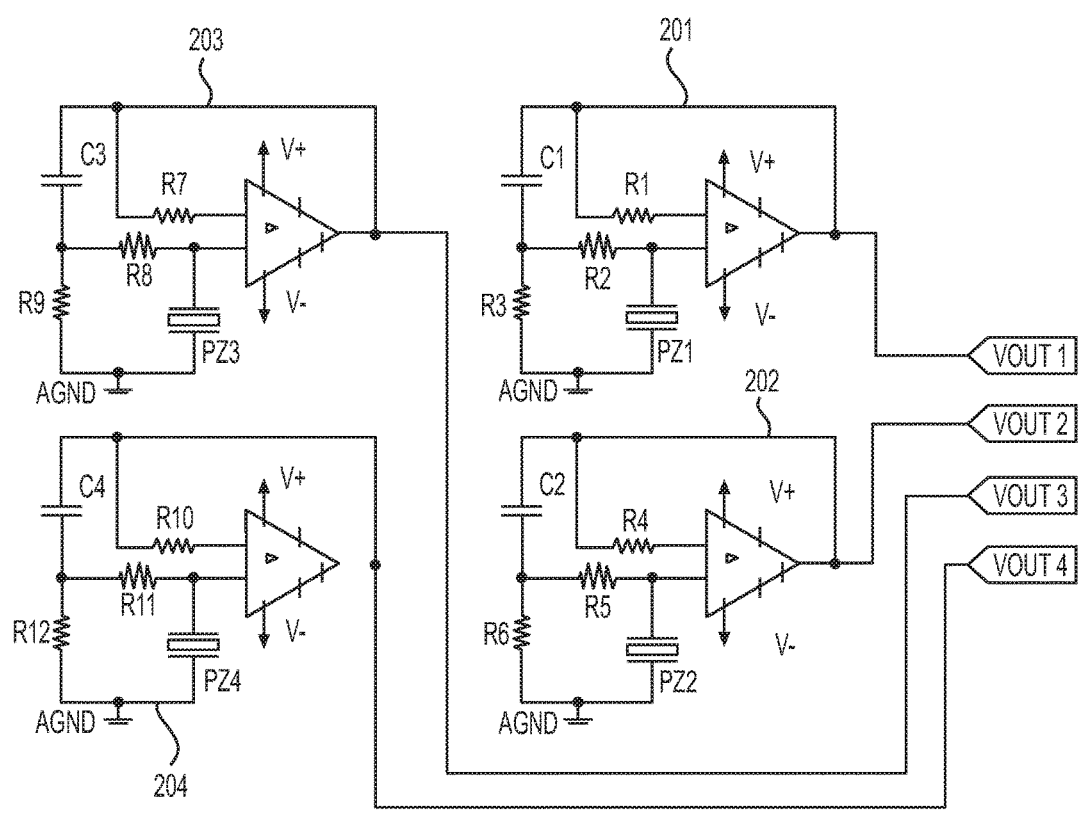
FIG. 11 shows an electronic circuit that can be used to read the output generated by the one or more touch or motion sensors.

FIG. 11 shows an electronic circuit that can be used to read the output generated by the one or more touch or motion sensors 201, 202, 203, 204. In some embodiments, one or more operational amplifiers can be used to condition the signal generated by one or more of the sensors 201, 202, 203, 204 to make it readable by further electronics. The same circuit can be duplicated to read other sensors as well.

While the embodiments described above illustrate an IPG device having certain features (e.g., four touch sensors), one skilled in the art will appreciate that the IPG device can have less than or greater than four touch sensors. In addition, the sensors can be a variety of touch and/or motion sensors. Furthermore, as noted above, the touch and/or motions sensors can be provided in conjunction with the IPGs wireless capabilities, thereby providing different means to generate an output by the IPG.

While the invention herein disclosed has been described by means of specific embodiments and applications thereof, numerous modifications and variations can be made thereto by those skilled in the art without departing from the scope of the invention.

What is claimed is:

1. A system for exerting pulses to a targeted site within a body comprising:
    an implantable pulse generator, wherein the implantable pulse generator comprises:
        a casing housing a circuit board, wherein the circuit board contains circuitry comprising a microcontroller and an ASIC, wherein the microcontroller is configured to receive signals generated from a wireless remote control and a touching force, wherein the ASIC is configured to receive data from the microcontroller to generate electrical signals; and
        a lead contact assembly operably connected to the ASIC, wherein the lead contact assembly comprises a plurality of leads that are used to carry electrical signals from the IPG to the targeted site within the body
        wherein the circuit board further comprises at least one touch sensor for generating a signal based on the touching force,
        wherein the circuit board further comprises at least four touch sensors for generating a signal based on the touching force,
        wherein the at least four touch sensors are configured to generate a signal when they are touched sequentially in a clockwise direction.

2. The system of claim 1, wherein the at least one touch signal generates a signal that is received into the microcontroller.

3. The system of claim 1, wherein the lead contact assembly comprises at least one set screw for securing the plurality of leads to other components of the IPG.

4. The system of claim 1, wherein the implantable pulse generator comprises at least one accelerometer.

5. The system of claim 1, further comprising an external remote control for generating a signal within the IPG.

6. The system of claim 1, wherein the implantable pulse generator comprises at least a pair of touch and motion sensors.

7. The system of claim 6, wherein the pair of touch and motion sensors send signals into the microcontroller.

8. A system for exerting pulses to a targeted site within a body comprising:
    an implantable pulse generator, wherein the implantable pulse generator comprises:
        a casing housing a circuit board, wherein the circuit board contains circuitry comprising a microcontroller and an ASIC, wherein the microcontroller is configured to receive signals generated from a touching force, wherein the ASIC is configured to receive data from the microcontroller to generate electrical signals; and
        a lead contact assembly operably connected to the ASIC, wherein the lead contact assembly comprises a plurality of leads that are used to carry electrical signals from the IPG to the targeted site within the body wherein the circuit board further comprises at least four touch sensors for generating a signal based on the touching force
wherein the at least four touch sensors are configured to generate a signal when they are touched sequentially in a clockwise direction.

9. The system of claim 8, wherein the circuit board further comprises at least one touch sensor for generating a signal based on the touching force, wherein the at least one touch signal generates a signal that is received into the microcontroller.

10. The system of claim 8, wherein the plurality of leads are sized and configured to extend into an epidural for spinal cord stimulation.

11. The system of claim 8, wherein the lead contact assembly comprises at least one set screw for securing the plurality of leads to other components of the IPG.

12. The system of claim 8, wherein the implantable pulse generator comprises at least one accelerometer.

13. The system of claim 8, further comprising an external remote control for generating a signal within the IPG.

14. The system of claim 8, wherein the implantable pulse generator comprises at least a pair of touch and motion sensors.

15. The system of claim 14, wherein the pair of touch and motion sensors send signals into the microcontroller.

* * * * *